(12) United States Patent
Fray et al.

(10) Patent No.: US 7,297,677 B2
(45) Date of Patent: Nov. 20, 2007

(54) METHOD OF IMPROVING THE SKIN BARRIER FUNCTION OF A PET

(75) Inventors: Timothy Richard Fray, Leicestershire (GB); Peter John Markwell, Leicestershire (GB); Adrian Leslie Watson, Leicestershire (GB)

(73) Assignee: Mars Incorporated, McLean, VA (US)

( * ) Notice: Subject to any disclaimer, the term of this patent is extended or adjusted under 35 U.S.C. 154(b) by 0 days.

(21) Appl. No.: 10/545,102

(22) PCT Filed: Feb. 12, 2004

(86) PCT No.: PCT/GB2004/000539

§ 371 (c)(1),
(2), (4) Date: Apr. 18, 2006

(87) PCT Pub. No.: WO2004/071208

PCT Pub. Date: Aug. 26, 2004

(65) Prior Publication Data

US 2006/0204552 A1    Sep. 14, 2006

(30) Foreign Application Priority Data

Feb. 14, 2003  (GB) .................................. 0303478.2
Dec. 18, 2003  (GB) .................................. 0329320.6

(51) Int. Cl.
    *A23K 1/00* (2006.01)
(52) U.S. Cl. ................. 514/2; 426/2; 424/442
(58) Field of Classification Search ............... None
    See application file for complete search history.

(56) References Cited

U.S. PATENT DOCUMENTS

| | | | |
|---|---|---|---|
| 3,219,454 A | 11/1965 | Jacobsen et al. | |
| 4,265,913 A * | 5/1981 | Eichelburg | ................. 426/2 |
| 4,275,154 A | 6/1981 | Hall | |
| 4,885,157 A | 12/1989 | Fiaschetti | |
| 5,053,230 A | 10/1991 | Gazzani | |
| 5,536,645 A | 7/1996 | Jay | |
| 6,020,351 A * | 2/2000 | Pero | ................. 514/355 |
| 6,245,803 B1 | 6/2001 | Acosta et al. | |
| 6,306,453 B1 | 10/2001 | Kuerzinger | |

FOREIGN PATENT DOCUMENTS

| | | |
|---|---|---|
| GB | 729 974 | 5/1955 |
| GB | 2 385 766 | 9/2003 |
| WO | WO-91/10726 | 7/1991 |

OTHER PUBLICATIONS

Association of American Feed Control Officials Incorporated, Official Feed Terms, 1996, p. 161.
National Research Council, "Nutrient Requirements of Dogs," Academy Press, 1985.
Rainbird, "A Balanced Diet," In: *Waltham Book of Dog and Cat Nutrition*, ATB Edney, Ed., 57-74, 1988.
Search Report for United Kingdom Patent Application No. 0303478.2.
Search Report for PCT/GB2004/000539.

* cited by examiner

*Primary Examiner*—Cecilia J. Tsang
*Assistant Examiner*—Ronald T Niebauer
(74) *Attorney, Agent, or Firm*—Fulbright & Jaworski LLP

(57) ABSTRACT

The present invention provides a composition preferably a pet foodstuff comprising pantothenic acid, nicotinamide, histidine, inositol and choline wherein pantothenic acid is provided at a level of 10 mg to 500 mg per 400 kcal per day, its use in the treatment of a skin disorder and methods of controlling a skin disorder. The invention further provides a method of manufacturing a composition of the invention.

11 Claims, 10 Drawing Sheets

METHOD OF IMPROVING THE SKIN BARRIER FUNCTION OF A PET

The present invention provides a composition comprising pantothenic acid, nicotinamide, histidine, inositol and choline, its use in the treatment of a skin disorder and methods of controlling a skin disorder. The invention further provides a method of manufacturing a composition of the invention.

In most household pets, a healthy skin and coat indicates an animal in general good health. As the skin and coat condition of a pet provides such an important visual impact (in particular to pet owners and/or to the public in general) it is, an ongoing aim in the art to improve the skin and hair conditions of animals, in particular where an animal suffers from a skin disorder.

Canine skin disease is the single most common reason for a pet to be taken to a veterinary practice. It is suggested that the proportion of animals suffering from such diseases account for in the order of 15% of the workload of such practices. The main conditions which contribute to this statistic are flea allergic dermatitis, atopic (allergic) dermatitis, pyoderma (bacterial infection), seborrhea and mange (demodectic and sarcoptic). In the majority of these skin diseases, the barrier properties of the skin are substantially compromised.

The primary role of the mammalian epidermis is to provide a barrier which protects the body from potentially damaging environmental influences, including a desiccating atmosphere, physical trauma and frequent contact with allergens, irritants and toxic agents. The outermost 'cornified' stratum corneum (SC) of the epidermis plays the principle role of barrier defence. The SC is formed by the terminal differentiation of the main skin cell-type known as the keratinocyte. The terminal differentiation process includes four essential steps: keratinisation, keratohyalin deposition, formation of an insoluble peripheral envelope and the generation of intercellular domains from the exocytosed lipid-rich lamellar bodies.

The process of barrier formation is inextricably linked to control of cell differentiation. This is, in turn, dependent on the hydration state of the skin. Thus, any disturbance to the epidermis which results in an increased transepidermal water loss (TEWL) will disturb hydration levels and in turn perturb many aspects of cell behaviour. A consequence of this can be poor skin structure leading to bacterial infection, penetration of allergens or toxic materials as well as increased water loss further exacerbating the condition.

The present invention provides a composition which can be used to improve the natural barrier defences of the skin. The composition enhances the skin's natural resistance to disease as well as aiding recovery from disease.

The first aspect of the present invention provides a composition comprising pantothenic acid, nicotinamide, histidine, inositol and choline, wherein pantothenic acid is provided at a level of 10 to 500 mg/400 kcal per day.

In a preferred feature of the first aspect, the composition is provided as a foodstuff preferably a pet foodstuff comprising pantothenic acid, nicotinamide, histidine, inositol and choline, wherein pantothenic acid is provided at a level of 10 to 500 mg/400 kcal per day. All preferred features discussed in relation to a composition of the invention also apply to the foodstuff of the invention and vice versa.

The foodstuff of the first aspect comprises pantothenic acid at a level (all per 400 kcal) of approximately 10 mg to approximately 500 mg, preferably approximately 10 mg to approximately 100 mg, more preferably at a level of approximately 10 mg to approximately 40 mg, more preferably approximately 12 mg to approximately 35 mg per day. Pantothenic acid is most preferably provided at a level of approximately 15 mg to approximately 20 mg per day. Pantothenic acid is present in the body in the form of co-enzyme A. Co-enzyme A is required for any chemical reactions which generate energy. Pantothenic acid is involved in epidermal lipid synthesis. Furthermore, it has been suggested that administration of pantothenic acid either orally or topically as an ointment accelerates the closure of skin wounds and increases the strength of scar tissue.

The pantothenic acid can be provided from liver, kidney, yeast, egg yolk and broccoli. Other sources of pantothenic acid include fish, shellfish, chicken, milk, yogurt, legumes, mushrooms, avocado and sweet potato.

For the present invention, pantothenic acid is preferably provided in an isolated form as a solid or a semi-solid supplement, more preferably as a powder. Pantothenic acid is preferably provided as di-calcium panthothenate.

The foodstuff of the first aspect comprises nicotinamide. For the purposes of this invention, a reference to the term nicotinamide includes niacin and nicotinic acid. Nicotinamide is used in the body to form the co-enzymes nicotinamide adenine dinucleotide (NAD) and nicotinamide adenine dinucleotide phosphate (NADP). Nicotinamide can be synthesised in the liver from tryptophan. Nicotinamide has been shown to increase epidermal ceramide synthesis.

The nicotinamide can be provided by yeast, meat, poultry, fish, cereals, legumes and seeds. Alternatively, nicotinamide can be provided in an isolated form as a solid or semi-solid, preferably as a powder.

The foodstuff of the first aspect preferably provides nicotinamide at a level (all per 400 kcal) of approximately 25 mg to approximately 800 mg, preferably approximately 35 mg to approximately 500 mg per day, more preferably approximately 35 mg to 200 mg, more preferably approximately 50 mg to approximately 150 mg, most preferably approximately 100 mg or above per day.

The foodstuff of the first aspect comprises histidine. Histidine has been shown to increase epidermal ceramide synthesis. It is postulated that histidine is involved in the differentiation pathway of keratinocytes. In addition histidine is essential for neonates and its deficiency results in delayed growth and eczema of the skin. Histidine has a role in the formation of hemoglobin, in the promotion of leucocyte formation and is involved in the growth and repair of tissue.

Histidine can be provided as the isolated or partially isolated amino acid, or as a salt or derivative thereof. Histidine can be provided as a solid or semi-solid, preferably as a powder. Sources of histidine can include meat, poultry, dairy fish, rice wheat and rye.

The foodstuff of the first aspect preferably provides histidine at a level (all per 400 kcal) of approximately 10 mg to approximately 10000 mg, preferably approximately 400 mg to approximately 1600 mg, more preferably approximately 50 mg to approximately 1100 mg per day, more preferably approximately 600 mg to approximately 1100 mg, most preferably approximately 900 mg to approximately 1100 mg per day.

The foodstuff of the first aspect comprises inositol. Inositol is a fundamental ingredient of cell membranes and is necessary for proper nerve, brain and muscle function. Inositol is also involved in increasing ceramide synthesis.

The inositol can be provided in an isolated form as a solid or semi solid. Preferably inositol is provided as a powder. Inositol can alternatively be provided as inositol monophosphate. Sources of inositol for the present invention include beans, liver, cantaloupe, citrus fruits (except lemons), chick peas, lecithin granules, lentils, nuts, oats, pork, rice, veal, wheat germ and whole grain products.

The foodstuff of the first aspect preferably provides inositol at a level (all per 400 kcal) of approximately 10 mg to approximately 500 mg, preferably approximately 50 mg to approximately 300 mg, more preferably approximately 100 mg to approximately 230 mg, most preferably approximately 185 mg to approximately 200 mg per day.

The composition of the first aspect comprises choline. Choline is involved in increasing epidermal ceramide synthesis. The choline can be provided as choline silica.

The foodstuff of the first aspect preferably provides choline at a level (all per 400 kcal) of approximately 10 mg to approximately 700 mg, preferably approximately 100 mg to approximately 400 mg, more preferably at a level of approximately 250 mg to approximately 360 mg, most preferably approximately 300 mg to approximately 330 mg per day.

In a particular preferred feature of the first aspect, there is provided a foodstuff comprising pantothenic acid, nicotinamide, histidine, inositol and choline, wherein pantothenic acid is provided at a level of 10 to 500 mg/400 kcal per day and one or more of the additional components is provided at a respective level provided below;

| Component | Level (mg/400 kcal per day) |
|---|---|
| Nicotinamide | 25-800 |
| Histidine | 10-10000 |
| Inositol | 10-500 |
| Choline | 10-700 |

Preferably, two or more of the components can be provided at the respective levels indicated above, more preferably three or more of the components are provided at the respective levels indicated above, most preferably four or more of the components are provided at the respective levels indicated above.

The foodstuff may optionally comprise one or more of pyridoxine, proline, one or more fatty acids or linoleic acid.

The foodstuff of the first aspect may optionally comprise pyridoxine. Pyridoxine is involved as a co-enzyme in many chemical reactions in the body including gluconeogenesis, synthesis of serotonin in the brain and the synthesis of heme. Pyridoxine is also known to increase epidermal ceramide synthesis.

For the purposes of this invention, the term pyridoxine also relates to pyridoxal, pyridoxamine and phosphate derivatives of pyridoxal, pyridoxamine and pyridoxine. Sources of pyridoxine include chicken, turkey, salmon, banana, potato, spinach, hazelnuts and other vegetables. Pyridoxine is preferably provided as free pyridoxine, or a salt or derivative thereof and is provided as a solid or semi-solid. Pyridoxine is preferably provided as a powder. Preferably pyridoxine is provided as pyridoxine hydrochloride.

The foodstuff of the first aspect optionally provides pyridoxine at a level (all per 400 kcal) of approximately 1 mg to approximately 500 mg, preferably approximately 10 mg to approximately 100 mg, more preferably approximately 8 mg to 20 mg per day, most preferably approximately 8 mg or above per day.

The foodstuff of the first aspect may optionally comprise proline. Proline has been shown to increase ceramide synthesis. It is postulated that proline is involved in the differentiation pathway of keratinocytes. In addition, proline has been shown to improve skin texture, aid collagen formation and to help contain the loss of collagen during ageing. Proline has also been shown to be important in the maintenance of muscle, joints and tendons.

The proline can be provided as the free amino acid or as a salt or a derivative thereof. Sources of proline include meat, dairy, eggs, poultry or wheat. Proline is preferably provided as gelatin.

The foodstuff of the first aspect optionally provides proline at a level (all per 400 kcal) of approximately 0.1 g to approximately 20 g, preferably approximately 0.5 g to approximately 5 g, more preferably at a level of approximately 2 g to approximately 3 g per day.

The foodstuff of the first aspect may comprise one or more polyunsaturated fatty acids. The polyunsaturated fatty acids may include one or more omega-3 fatty acids (which include eicosapentaenoic acid (EPA), docasahexaenoic acid (DHA) or alpha-linolenic acid (ALA)) or one or more omega-6 fatty acids (which include gamma-linolenic acid (GLA)). Each of the fatty acids may be provided in a purified form or by one or more of fish oil, soya oil, blackcurrant oil, sunflower oil or ground nut oil. The fatty acids can further be obtained from flaxseed.

Polyunsaturated fatty acids are anti-inflammatory and anti-oxidant compounds. They are useful in the treatment of atopy, flea allergic dermatitis and pruritus.

The foodstuff of the first aspect may optionally comprise linoleic acid. Linoleic acid is beneficial to epidermal ceramide synthesis.

The foodstuff of the first aspect optionally provides one or more fatty acids at levels of approximately 10 mg to approximately 1000 mg per 400 kcal preferably from approximately 50 mg to approximately 500 mg per 400 kcal, more preferably approximately 200 mg per 400 kcal per day or above. Most preferably, eicosapentaenoic acid is provided at a level of approximately 300 mg per 400 kcal or above and/or docasahexaenoic acid is provided at a level of approximately 200 mg per 400 kcal or above.

The present invention relates, for all aspects, to any animal. The invention relates, in particular, to humans, horses, cats (e.g. *Felis domesticus*, the domestic cat) and most preferably to dogs (e.g. *Canis doinesticus*, the domestic dog).

The foodstuff according to the preferred feature of the present invention encompasses any product that a animal consumes in its diet. In particular, the product is a pet food, more particularly a cat or a dog food. Thus, the invention covers standard food products as well as pet food snacks (for example, snack bars, biscuits, drinks and sweet products). The foodstuff is preferably a cooked product. It may incorporate meat or animal derived material (such as beef, chicken, turkey, lamb, fish, blood plasma, marrow bone etc or one or more thereof). The product alternatively may be meat free (preferably including a meat substitute such as soya, maize gluten or a soya product) in order to provide a protein source. The product may contain additional protein sources such as soya protein concentrate, milk proteins, gluten etc. Preferably, the protein source is a selected protein such as one or more of chicken, rice, catfish, capelin, tapioca or mehaden. For the purposes of this invention, a selected protein is a protein derived from a minimum number of ingredients, where the ingredients are not commonly associated with sensitivity reactions.

The product may also contain a starch source such as one or more grains (e.g. corn, rice, oats, barley etc), or may be starch free. It may include a gelatinised starch matrix.

The foodstuff of the invention may be a dry product (with approximately 5 to 12% moisture), a semi-moist product (with approximately 12 to 70% moisture) or a wet product (with approximately 70 to 90% moisture).

The foodstuff is preferably packaged. In this way, the consumer is able to identify, from the packaging, the ingredients in the foodstuff and confirm that it is suitable for the particular pet in question. The packaging may be metal (usually in the form of a tin or flexifoil), plastic (usually in the form of a pouch or bottle), paper or card. The amount of moisture in any product may influence the type of packaging, which can be used or is required.

The foodstuff of the invention is preferably a complete and balanced food or is preferably used in combination with a complete and balanced food (for example, as described in National Research Council, 1985, Nutritional Requirements for Dogs, National Academy Press, Washington D.C. or Association of American Feed Control Officials, Official Publication 1996). A complete and balanced diet includes a high quality commercial food. A high quality commercial food can be defined as a diet manufactured to the nutrient recommendations of the National Research Council, 1985 (supra), wherein the digestibility of key nutrients is 80% or more.

The concentrations of the components to be added to the foodstuff are calculated on the basis of the energy content of the foodstuff and of any additional nutrients which may be consumed by the animal. Preferably, a complete and balanced food, (including a high quality commercial food) comprises the foodstuff according to the invention.

The foodstuff of the first aspect can be provided as a food supplement. The food supplement can be a powder, biscuit, kibble, sauce, topping, pocket or tablet that can be administered with or without an additional foodstuff. Where the food supplement is administered with an additional foodstuff, the food supplement can be administered sequentially simultaneously or separately. The food supplement may be mixed with the foodstuff, sprinkled or poured over the foodstuff or served separately. Alternatively, the food supplement can be added to a liquid provided for drinking such as water or milk.

The foodstuff of the first aspect may be provided as a commercial product, which will be available from commercial outlets and/or from veterinary surgeons.

In an alternative feature of the first aspect, the composition of the invention can be provided for administration by any convenient method including orally (including by inhalation), parenteral, mucosal (such as buccal, sublingual, nasal), rectal, transdermal or topical. In this feature of the first aspect the composition is preferably not a foodstuff.

The composition of the first aspect of the invention, can be provided as a formulation which is applied externally to the skin surface. The composition can be in the form of a cream or lotion (including oil in water and water in oil creams and lotions), spray, powder, gel, shampoo, conditioner, mousse, serum, oil, stick, patch, humectant or occlusive.

The second aspect of the invention provides a composition as defined in the first aspect of the invention for use in improving skin barrier function. In a preferred feature, the second aspect relates to a foodstuff as defined in the first aspect of the invention for maintaining and/or improving skin barrier function in particular wherein the skin is affected by or is susceptible to, or is exposed to disease and/or trauma. Such improvement involves reducing the degree of transepidermal water loss and making the skin less susceptible to trauma and infection. The foodstuff of the second aspect therefore enhances the ability of the skin to resist disease and/or trauma, and/or reduces the degree of transepidermal water loss. The foodstuff can be provided to an animal with impaired or reduced skin barrier function, to an animal which is susceptible to impaired or reduced skin barrier function or to an animal who will or who it is envisage will undergo a trauma to the barrier of the skin.

The foodstuff of the first aspect promotes the increased formation of the barrier enhancing lipids which exist between differentiating skin cells. Furthermore, the foodstuff maintains the barrier enhancing lipids during periods of stress such as hot or cold conditions, following shampooing etc. This improvement in the skin barrier will prevent harmful environmental agents from penetrating the skin or from penetrating the skin deeply enough to be dangerous, thus making the skin less susceptible to disease. The foodstuff of the first aspect maintains and/or increases barrier enhancing lipids in the skin. More preferably the foodstuff maintains and/or increases the formation of barrier enhancing lipids in the skin. The provision of improved or maintained skin barrier function allows the foodstuff of the first aspect to promote and/or aid the recovery of the skin from disease and/or trauma.

The foodstuff of the first aspect promotes and/or aids the recovery of skin lesions, skin abrasions, skin trauma associated with itching, damage due to scratching, and/or inflammation.

The second aspect of the invention further relates to the foodstuff of the first aspect for the prevention and/or treatment of a skin disorder. Such skin disorders include dermatological conditions which are associated with poor barrier function such as seborrhea, ichthyoses, eczema/atopic dermatitis, essential fatty acid disease and winter-induced xerosis. The second aspect preferably relates to a foodstuff for use in humans, dogs, cats and horses. In a preferred feature of the second aspect, the foodstuff is preferably a pet foodstuff which can be used to prevent or treat a skin disorder in a dog.

For the purposes of this invention, the terms "treating" or "treatment" mean to decrease or alleviate the symptoms suffered by an animal especially the symptoms of a skin disorder and/or assist in the management of a skin disorder. The terms "treatment" and "treating" further mean to promote or aid recovery of the skin for example to improve the appearance and condition of the skin. The terms "prevention" or "preventing" mean to stop the onset of symptoms or to reduce the severity of such symptoms suffered by an animal. In addition the terms "prevention" or "preventing" mean to delay the onset of symptoms.

Preferably the foodstuff is provided as an adjunct therapy and is preferably provided in combination with a conventional treatment. The foodstuff can be used separately, simultaneously or sequentially with the conventional treatment. Examples of such conventional treatments include the application of an emollient and/or hydrating cream or occlusion of the effected area. The conventional treatment may further involve the administration of a medicament by any convenient method including orally (including by inhalation), parenteral, mucosal (such as buccal, sublingual, nasal), rectal, transdermal or topical. The foodstuff of the second aspect can be used to promote or aid recovery of the skin, for example to improve the appearance and condition of the skin during or after conventional treatment.

The foodstuff of the invention may allow the reliance on conventional treatments such as drug therapy to be reduced. Alternatively the animal may exhibit less symptoms or the severity of the symptoms may be reduced. The animal may exhibit an improved level of well being.

Barrier function deterioration can often be a secondary effect of a primary condition or disease state such as an inflammatory disease. The foodstuff of the first aspect can therefore be used to treat side effects of a condition which affects skin barrier function. Where a medicament is used to treat a primary condition, the foodstuff of the first aspect can be used in combination with the medicament to treat the secondary deterioration in skin barrier function. The foodstuff of the first aspect can be used separately, simultaneously or sequentially with the medicament.

All preferred features of the first aspect, also apply to the second aspect.

The third aspect of the invention relates to the use of pantothenic acid, nicotinamide, histidine, inositol and choline in the manufacture of a composition for the prevention or treatment of a skin disorder wherein pantothenic acid is provided at a level of 10 mg to 500 mg/400 kcal per day. In a preferred feature of the third aspect, the composition is a pet foodstuff.

All preferred features of the first and second aspects, also apply to the third aspect.

The fourth aspect of the invention comprises a method of preventing or treating a skin disorder comprising administering a composition of the first aspect to an animal. In a preferred feature of the fourth aspect, the composition is a pet foodstuff. The animal may be in need thereof. Preferably, the animal is suffering from or has a predisposition to dermatological conditions which are associated with poor barrier function such as inflammatory skin disease, seborrhea, ichthyoses, eczema/atopic dermatitis, essential fatty acid disease or winter-induced xerosis.

For the purposes of the fourth aspect, the foodstuff is administered daily or twice daily. The foodstuff can be administered in combination with or in place of the animal's conventional food. The foodstuff can be provided as an adjunct therapy and is preferably provided in combination with a conventional therapy. For the purposes of this invention, the foodstuff can be provided with the conventional therapy to control the skin disorder or to treat a primary condition wherein the skin disorder is a secondary condition thereof. Additionally, the foodstuff can be provided after the course of conventional therapy has ended, in order to promote or aid the recovery of the skin by for example, aiding recovery of skin lesions, skin abrasions, skin trauma associated with itching, damage due to scratching, inflammation etc.

The fifth aspect of the invention relates to a method of producing a foodstuff as defined in the first aspect of the invention.

The foodstuff can be made according to any method known in the art such as in Waltham Book of Dog and Cat Nutrition, Ed. ATB Edney, Chapter by A. Rainbird, entitled "A Balanced Diet" in pages 57 to 74 Pergamon Press Oxford.

The components are added together at any time during the processing. They may all be added together at the same time, or individually, in any particular order. Other ingredients of the foodstuff may be added at any time during the processing. Preferably, two or more ingredients of the foodstuff are mixed together and then ground together. The moisture and temperature of the ground particles can be manipulated prior to any further processing step. The components may be added before or after any heating or cooking step. The processing may include shaping and/or packaging of the product. In a preferred feature of the fifth aspect, the product is shaped by extrusion to form pellets or kibbles. Extrusion preferably occurs at a pressure of 20-1000 psig and a temperature of 90-165° C.

Pantothenic acid, pyridoxine, nicotinamide, proline, histidine, inositol and choline may be mixed with the other components of the foodstuff or can be added to the completed foodstuff. One or more of pantothenic acid, nicotinamide, histidine, inositol and choline can be coated or sprayed on to the surface of the foodstuff. Alternatively, one or more of pantothenic acid, nicotinamide, histidine, inositol and choline are admixed, with one or more other components of the foodstuff. The final water content of the foodstuff can be manipulated using a cooler apparatus.

All preferred features of each of the aspects the invention apply to all other aspects mutatis mutandis.

The invention is described with reference to the figures in which;

FIG. 1 shows a one dimensional thin layer chromatograph of the lipid fraction from dermal fibroblasts (F) or differentiated keratinocytes (K) following incubation with $^{14}C$-serine. Each lane contains a Bligh-Dyer extract from $3\times10^5$ cells FIG. 2 shows ceramide synthesis by canine keratinocytes in vitro as measured by the incorporation of $^{14}C$-serine comparing control incubation with supplementation with nicotinamide FIG. 3 shows ceramide synthesis by canine keratinocytes in vitro as measured by the incorporation of $^{14}C$-serine comparing control incubation with supplementation with histidine or panthothenic acid FIG. 4 shows ceramide synthesis by canine keratinocytes in vitro as measured by the incorporation of $^{14}C$-serine comparing control incubation with supplementation with linoleic acid.

FIG. 5 shows ceramide synthesis by canine keratinocytes in vitro as measured by the incorporation of $^{14}C$-serine comparing control incubation with supplementation with pyridoxine FIG. 6 shows ceramide synthesis by canine keratinocytes in vitro as measured by the incorporation of $^{14}C$-serine comparing control incubation with supplementation with choline and inositol FIG. 7 shows ceramide synthesis by canine keratinocytes in vitro as measured by the incorporation of $^{14}C$-serine comparing control incubation with supplementation with nicotinamide or histidine FIG. 8 shows ceramide synthesis by canine keratinocytes in vitro as measured by the incorporation of $^{14}C$-serine comparing control incubation with supplementation with proline FIG. 9 shows total lipid synthesis by canine keratinocytes in vitro as measured by the incorporation of $^{14}C$-acetate comparing control incubation with supplementation with nicotinamide FIG. 10 shows total lipid synthesis by canine keratinocytes in vitro as measured by the incorporation of $^{14}C$-acetate comparing control incubation with supplementation with histidine or panthothenic acid FIG. 11a shows a photomicrograph of canine keratinocytes grown on a Costar Snapwell membrane and subsequently differentiated at the air-liquid interface. The photomicrograph was counterstained with Cresyl violet. Scale bar 40 micrometers FIG. 11b shows a transmission electron micrograph (TEM) of canine keratinocytes grown on a Costar Snapwell membrane and subsequently differentiated at the air-liquid interface. The photomicrograph was counterstained with lead citrate/uranyl acetate. Scale bar 2 micrometers FIG. 12 shows a photomicrograph of canine keratinocytes grown on a Costar Snapwell membrane, differentiated at the air-liquid interface and stained using Nile Red. The fluorescent staining shows the presence of neutral lipid in the stratified layer.

FIG. 13 shows trans-epidermal diffusion as measured by the rate of diffusion of tritiated water across a monolayer of keratinocytes in the presence (square) or absence (circle) of the keratinocytes FIG. 14 shows trans-epidermal diffusion as measured by the rate of diffusion of tritiated water across a layer of differentiated keratinocytes comparing the rate of diffusion in the presence of unsupplemented keratinocytes (diamond) with keratinocytes supplemented with pyridoxine (square)

The present invention will now be illustrated by reference to the following non-limiting examples.

EXAMPLES

Measurement of effect of the composition on the skin cells (Keratinocytes)

Obtaining Canine Keratinocytes

Canine keratinocytes were obtained via explant culture of skin samples taken from healthy adult animals (4 mm biopsy). Samples are washed and dissected in cold PBS containing antibiotics. The epidermis is dissected away from the dermis and cut into 1 $mm^2$ pieces. The pieces of epidermis are then placed into individual wells of a 24 well collagen-coated plastic plate and briefly allowed to dry down (60 seconds). Green's medium supplemented with 10% foetal bovine serum is then added and the explants cultured for 7-10 days until keratinocytes begin growing out of the edges of the skin. The primary skin cells are now detached from the plastic and explant tissue using trypsin and moved onto a i3T3 (irradiated fibroblast) feeder layer. Cells are expanded on the feeder layer until near confluent at which time they can be moved onto plastic alone. The primary keratinocytes can be used for assays at this point or further expanded in number as required.

In Vitro Lipid Synthesis Assays

Figure 1:
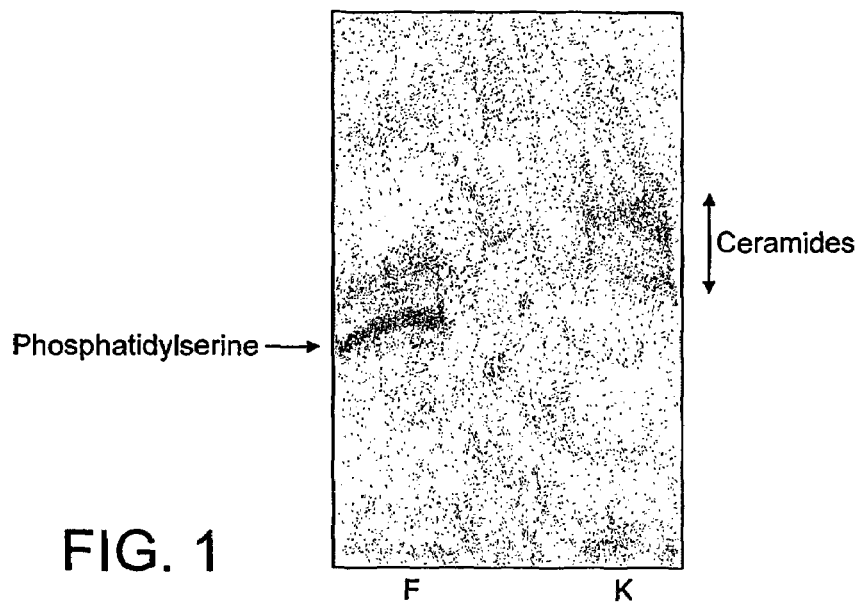
Figure 2:
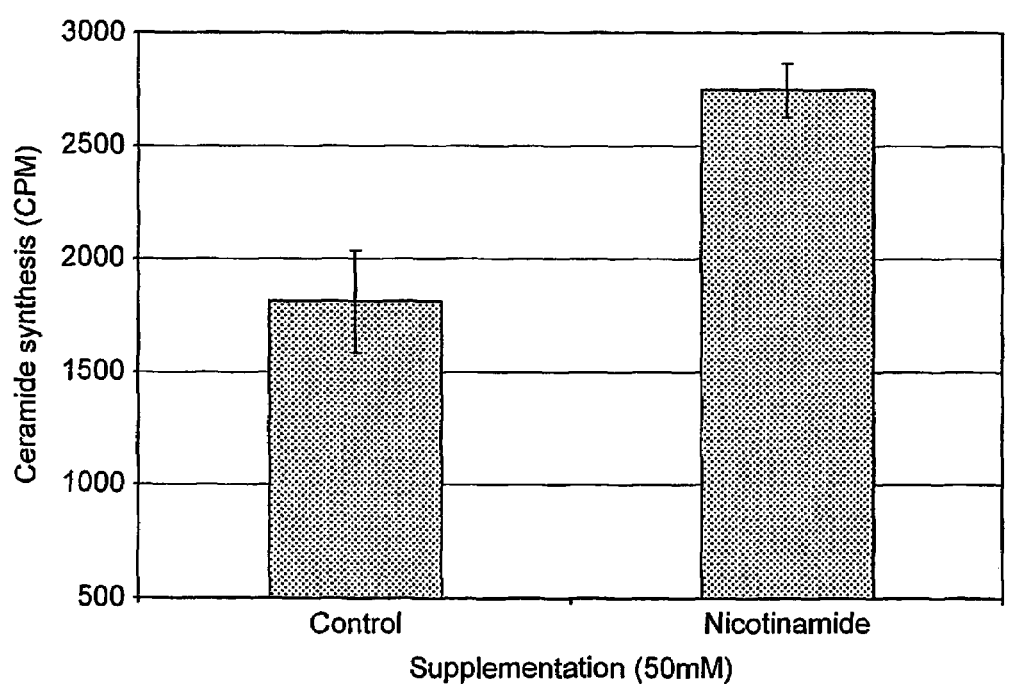
Figure 3:
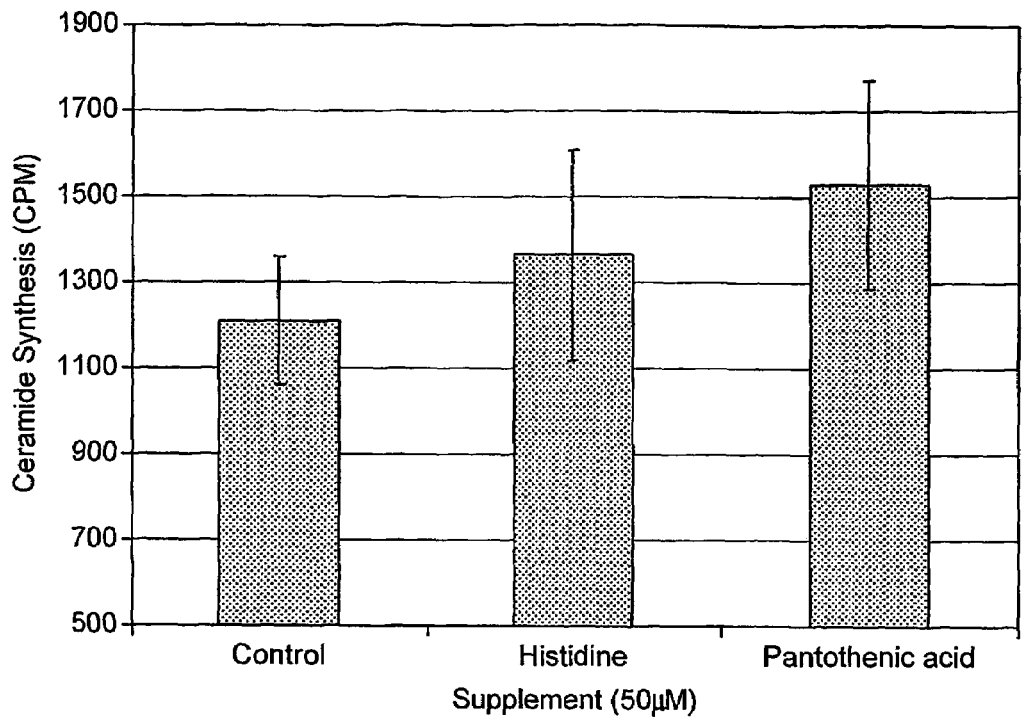
Figure 4:
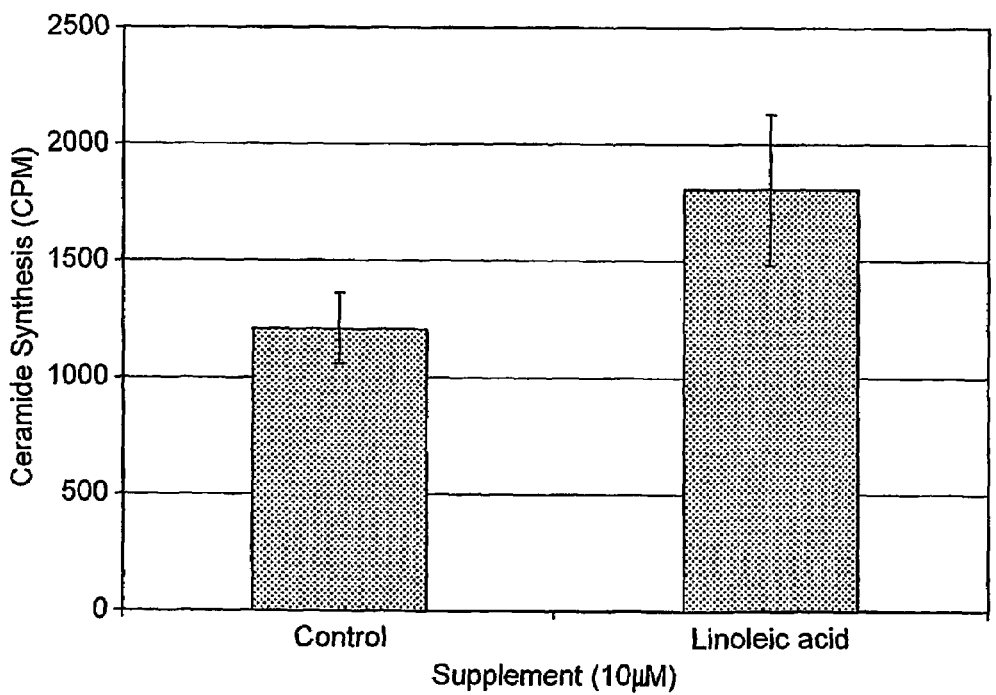
Figure 5:
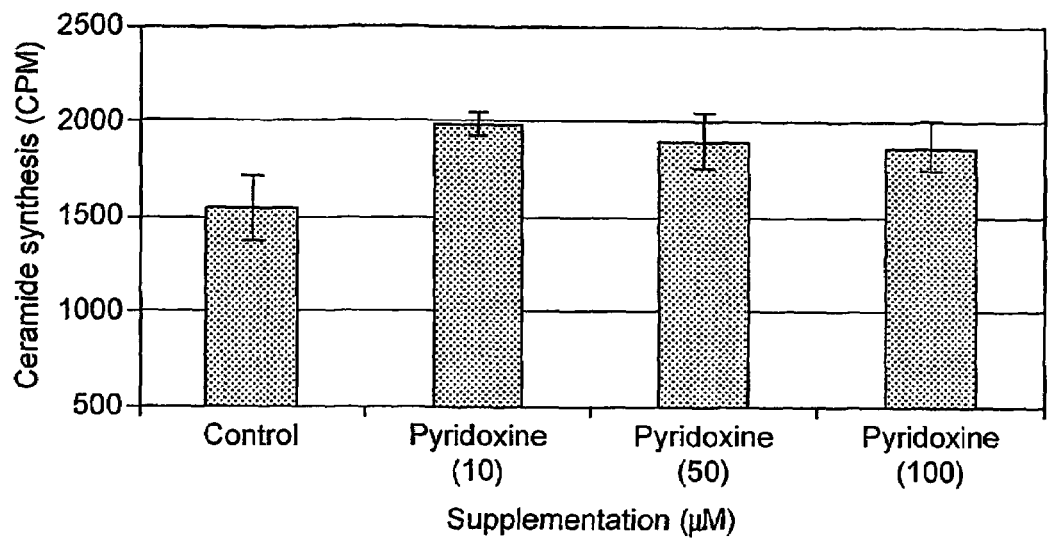
Figure 6:
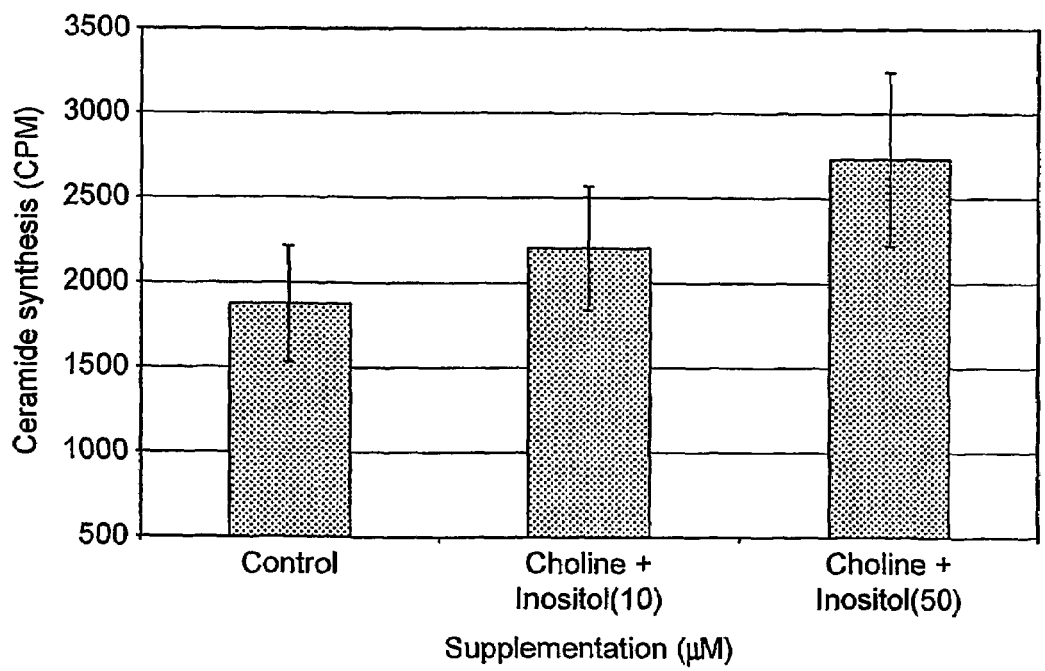
Figure 7:
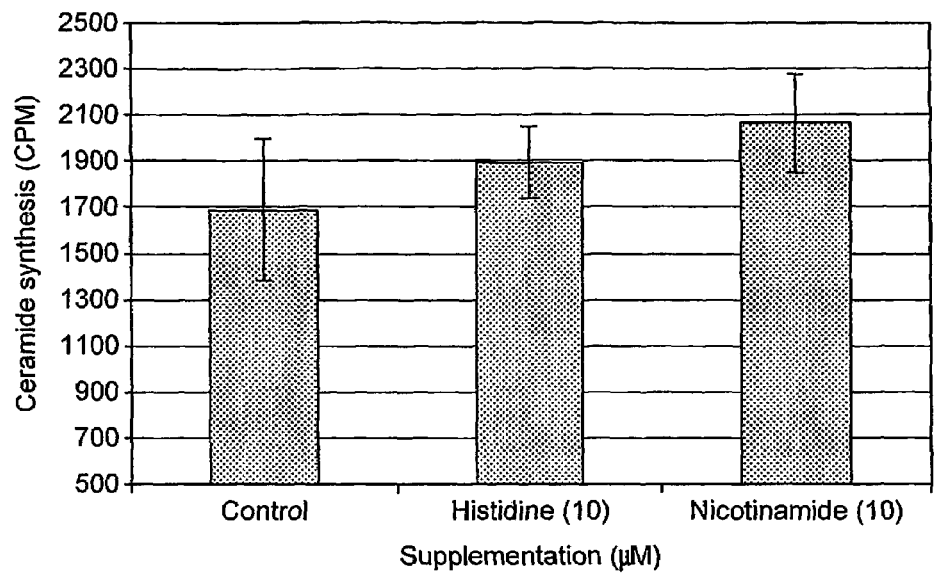
Figure 8:
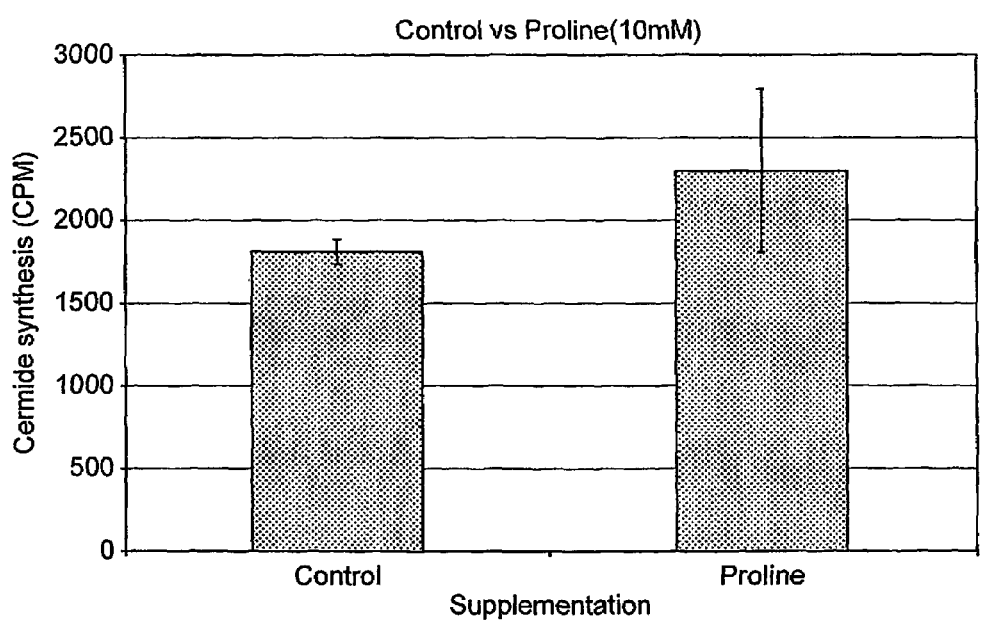

Keratinocytes are seeded in collagen-coated 24 well plates at a density of $5\times10^4$ cells per well. These cells are allowed to settle overnight and then the media changed. Cells are then left for 4 days under proliferation promoting culture conditions (in the presence of bovine pituitary extract). Following the 4 days the media is changed to one that promotes differentiation and at this stage the supplement to be tested is added (see individual experiments). Following 6 days under these conditions [$^{14}$C]-Serine is added for the ceramide assay or [$^{14}$C]-Acetate added for the total lipid assay, in both cases at 0.5 microCi per well. Cells are incubated in the presence of the radioactive markers and supplement for 2 days. At the end of the incubation period cells were harvested using trypsin and washed using PBS. Lipids were subsequently extracted using Bligh-Dyer solution and then added to 4 ml of scintillation fluid. The radioactivity was counted with a liquid scintillation spectrometer. Results for the ceramide synthesis assays are seen in FIGS. 1-6. Results for total lipid synthesis assays are seen in FIGS. 7-8.

In order to study the potential for nutritional supplementation to improve canine epidermal barrier function laboratory based screening assays were developed. These assays were designed in two different formats. The first set of assays focus on the influence of supplementation on the ability of skin cells (keratinocytes) to synthesise epidermal lipids and/or proliferate. The successful manufacture of skin lipids is intrinsic to the formation of an effective epidermal barrier. Adequate proliferation of keratinocytes is essential to provide new cells which replace those constantly lost due to sloughing off at the surface.

Barrier Function Diffusion Assay

Costar Snapwell plates (ASL Cat no. 402/0369/08) are set up containing 2.6 ml Greens Media in the outer well and 400 microliters Greens media in the inner well. The latter is seeded with $1\times10^5$ canine keratinocytes. These plates are incubated at 37° C., 5% $CO_2$. The Greens media in the inner well is changed after 24 hours to remove dead cells and the plates then cultured for a further 48 hours. Greens media is prepared containing test concentrations of supplements (see Table 1). On day three the media is removed from the inner and outer wells and 900 microliters of test/control media put into the outer well. The quantity of media added ensures that the keratinocytes are at the air-liquid interface. The plates are cultured for a further seven days with the media being replaced every two/three days. Two Snapwells were used per concentration of supplement and two per control.

Figure 9:
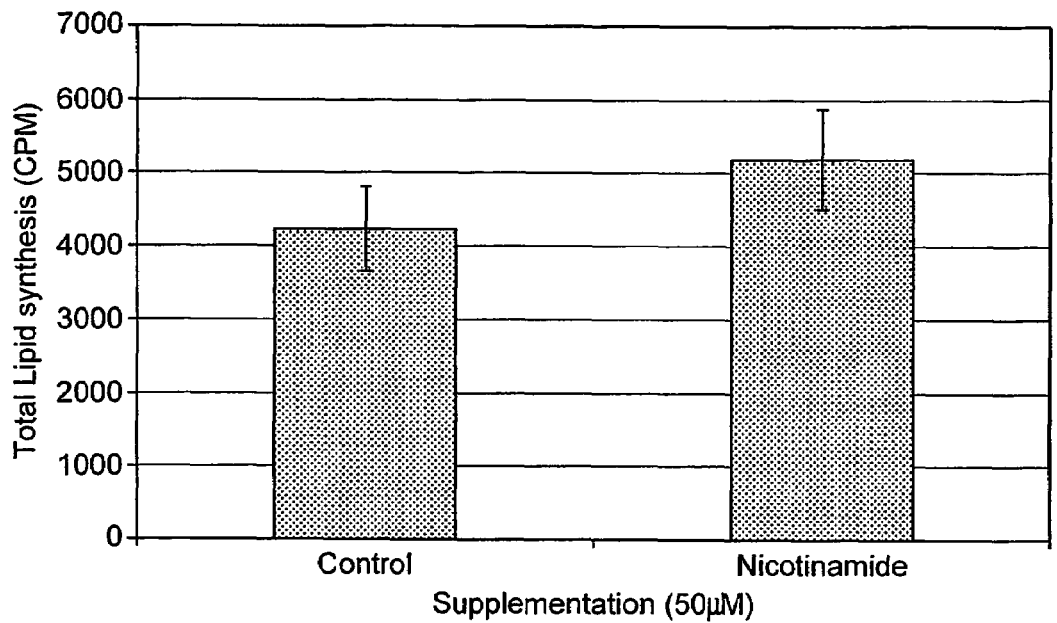
Figure 10:
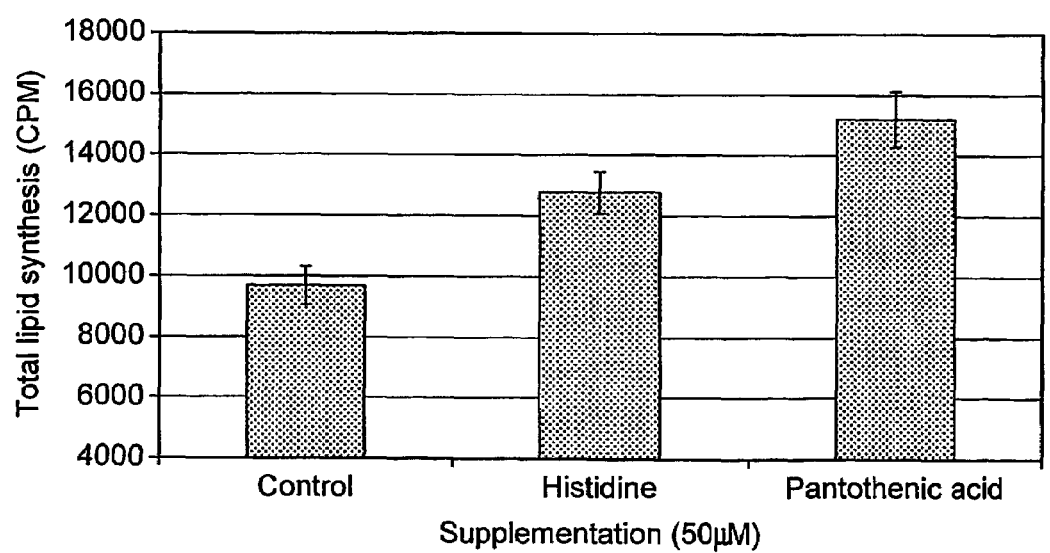

On day ten the Snapwells were ready for the diffusion assay. At this point the inner well of each Snapwell is removed and placed into individual diffusion chambers. Dulbecco's Modified Eagle's Medium (DMEM) is added to both sides of the chamber (6 ml per side), each chamber is then placed into the diffusion apparatus. This equilibrates the chambers to 37° C. and enables gas (5% $CO_2$ in air) to be continuously pumped through the chambers thus ensuring movement of the media. 100 microliters of radiolabelled water ($^3$H) is added to the left-hand side of each chamber and 50 microliters samples taken for 90 minutes at 3-minute intervals from the right hand side. DMEM (50 microliters) is replaced into the right hand side after each sample. Samples are then placed into scintillation vials containing 4 ml of scintillation fluid and the amount of radioactive label in each sample counted using a liquid scintillation spectrometer. The results for this assay are indicated in FIGS. 9-14. In addition to experiments whereby supplements have been tested in the presence of cells a control was performed in the absence of cells (FIG. 9).

The rate of diffusion across the skin barrier has been reduced in cells cultured in the presence of the foodstuff. This data indicates that incubation of the cells in the presence of the foodstuff reduced trans-epidermal water loss through the skin surface (as indicated by a decreased rate of diffusion). This data also shows that the foodstuff promoted the formation and optimisation of a functional skin barrier.

The second assay format is an in vitro barrier function diffusion assay. The system works by testing the diffusion rate of an aqueous radiolabelled marker across a barrier, in the form of a monolayer of keratinocytes. There is an inverse relation between the diffusion rate of the marker and the quality of the barrier formed by the keratinocytes. This is a near physiologic measure of barrier function.

Further detail of how the keratinocytes were obtained as well as the assay formats follows.

Keratinocyte Proliferation Assay

In order to test whether any of the supplements had the effect of increasing keratinocyte cell division a proliferation assay was performed. Cells are seeded at $5 \times 10^4$ per well in collagen coated plates and cultured under proliferation promoting conditions (with Bovine Pituitary Extract, BPE) for 72 hours. The medium is then changed to one without BPE and the supplements added in its stead. Following a further 24 hours 5 microliters of 3H-Thymidine is added (37 MBq/ml) to each well. Cells are incubated in the presence of radiolabel for 24 hours and then harvested with Trypsin. Following harvesting, cells were precipitated in cold 10% tricarboxylic acid (TCA), with two follow up washes of the pellet in cold 5% TCA. Finally the pellet was resuspended in scintillant and the radioactive incorporation counted using a liquid scintillation spectrometer.

Thin Layer Microscopy (TLC)

Figure 19:
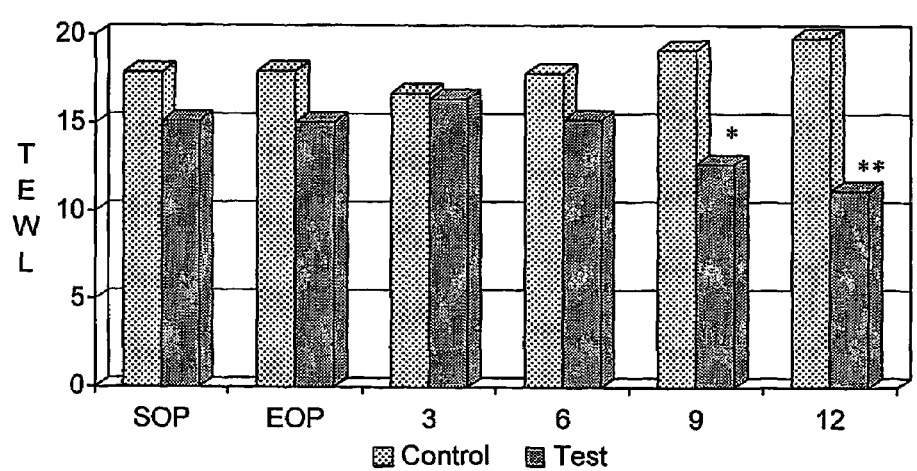
FIG. 19 shows transepidermal water loss (TEWL) in two groups of sixteen dogs, wherein the test dogs are supplemented with the composition and wherein; *$P<0.05$, **$P<0.01$ between groups SOP/EOP=start & end of prefeed; 3-12=weeks of supplementation. TEWL; $g/m^2$.hour.

FIG. 19 shows a TLC plate on which has been separated the Bligh-Dyer extracted lipid fraction of differentiated canine keratinocytes which had previously been incubated with 14C-Serine. Lane K shows the radiolabelled lipid fraction from keratinocytes. The bands were shown to be ceramides by comparison with non-radiolabelled standards run out on the same plate. The pattern of banding seen for a Bligh-Dyer extraction conducted on fibroblasts (Lane F) was different from that seen for the keratinocytes, most of the incorporation being seen for phosphatidylserine.

Microscopy Pictures

Figure 11:
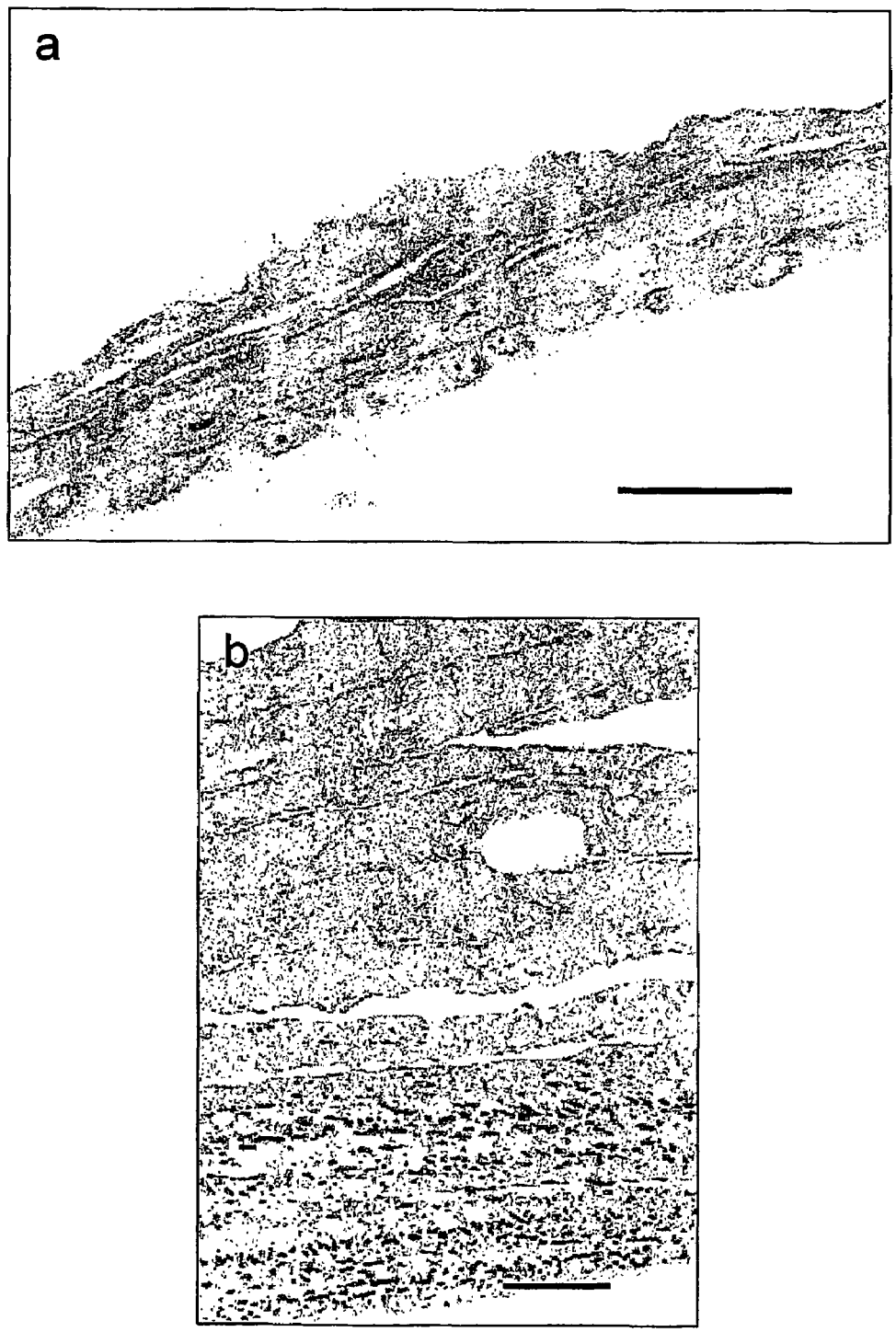
Figure 12:
Figure 13:
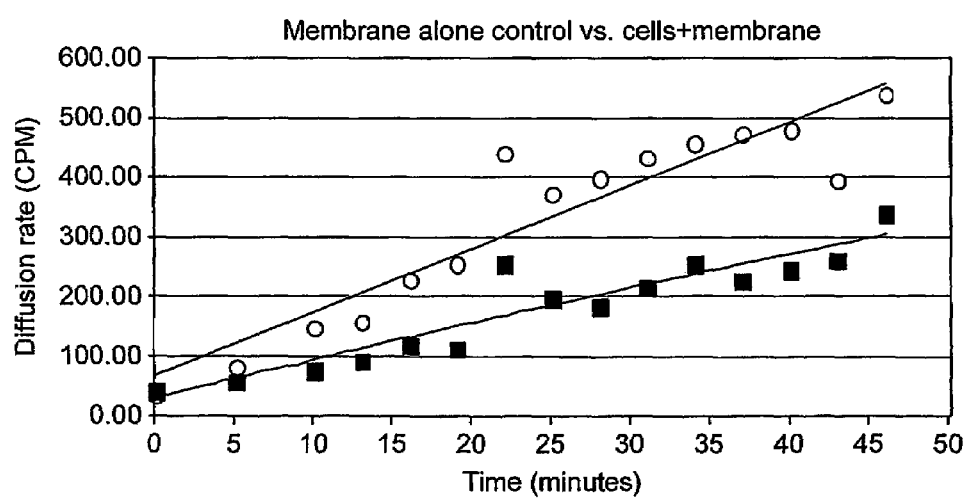
Figure 14:
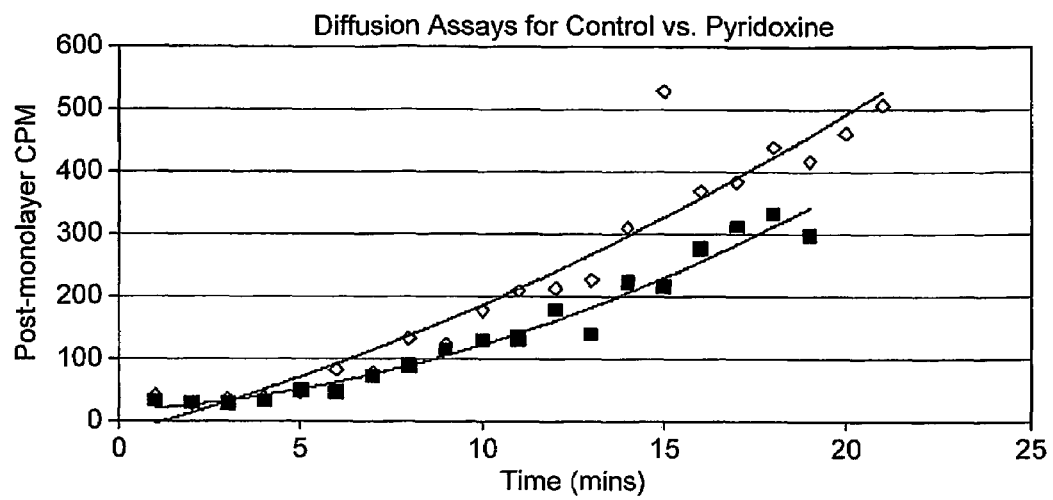
Figure 15:
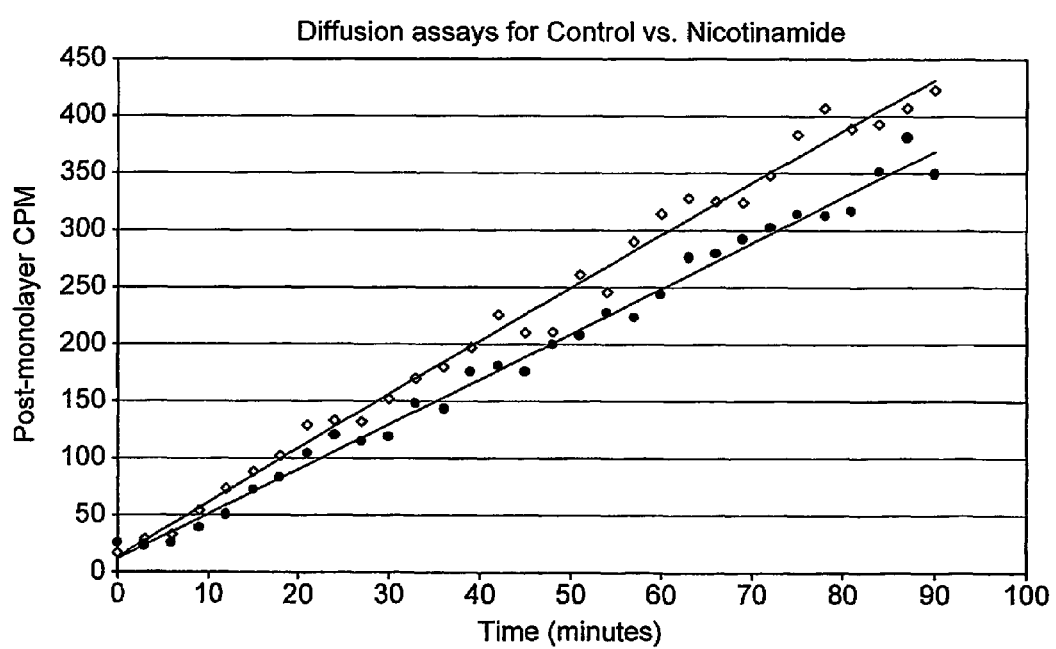
FIG. 15 shows trans-epidermal diffusion as measured by the rate of diffusion of tritiated water across a layer of differentiated keratinocytes comparing the rate of diffusion in the presence of unsupplemented keratinocytes (diamond) with keratinocytes supplemented with nicotinamide (circle)
Figure 16:
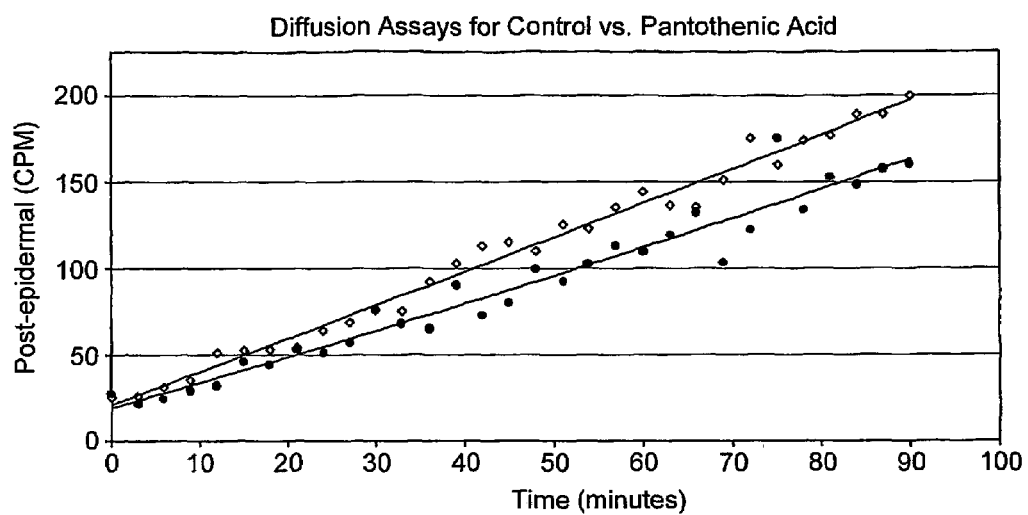
FIG. 16 shows trans-epidermal diffusion as measured by the rate of diffusion of tritiated water across a layer of differentiated keratinocytes comparing the rate of diffusion in the presence of unsupplemented keratinocytes (diamond) with keratinocytes supplemented with pantothenic acid (circle)
Figure 17:
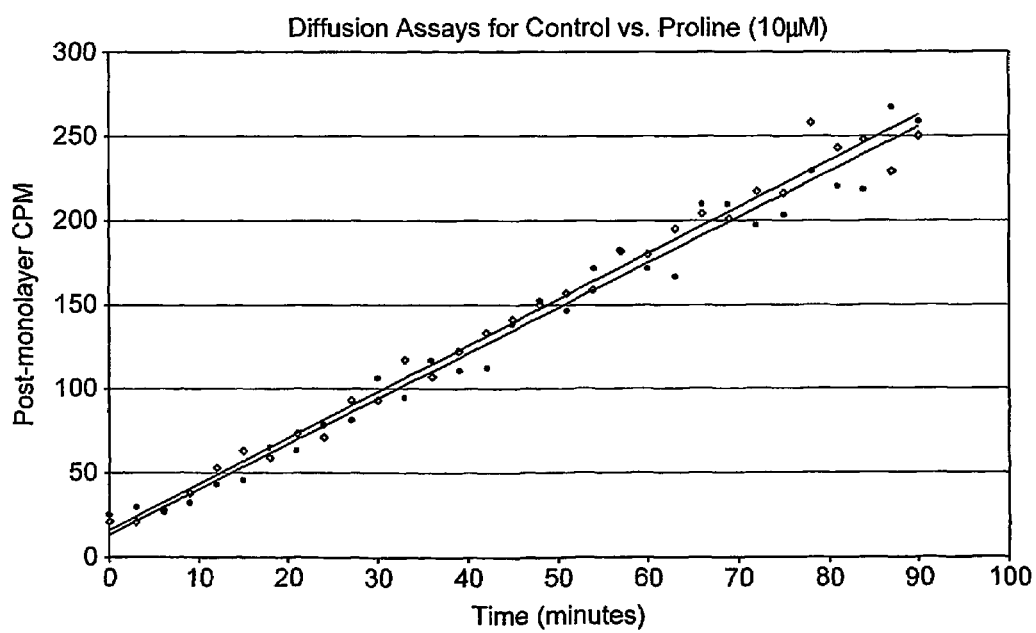
FIG. 17 shows trans-epidermal diffusion as measured by the rate of diffusion of tritiated water across a layer of differentiated keratinocytes comparing the rate of diffusion in the presence of unsupplemented keratinocytes (diamond) with keratinocytes supplemented with proline (circle).
Figure 18:
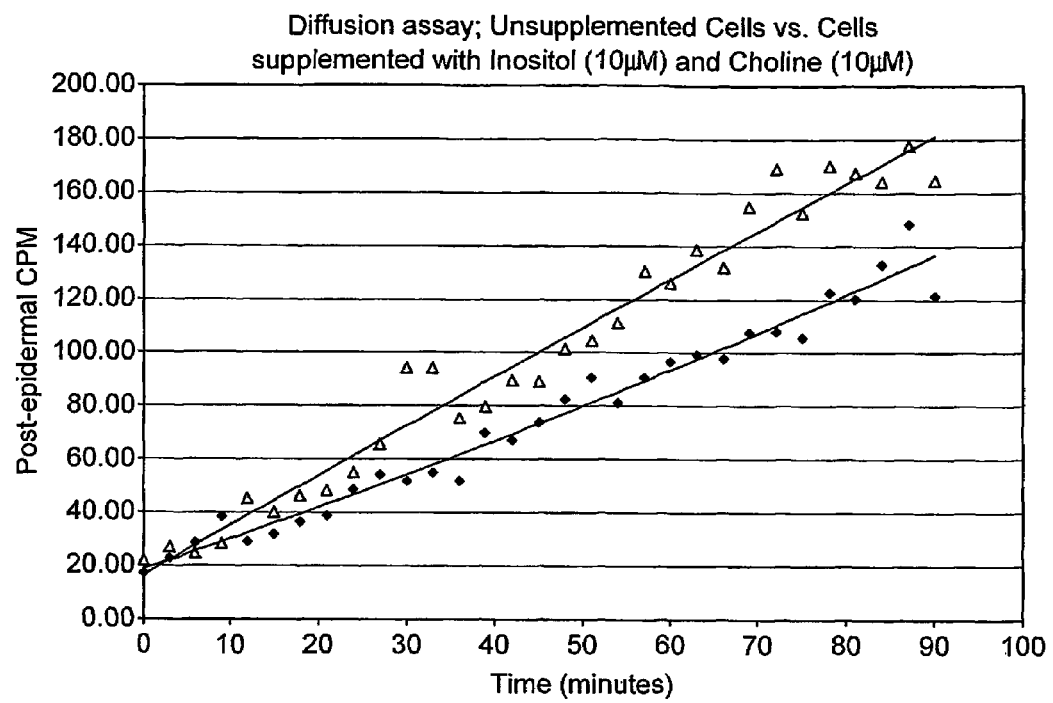
FIG. 18 shows trans-epidermal diffusion as measured by the rate of diffusion of tritiated water across a layer of differentiated keratinocytes comparing the rate of diffusion in the presence of unsupplemented keratinocytes (triangle) with keratinocytes supplemented with choline and inositol (diamond)

FIGS. 11a and 12 show micrographs taken from keratinocytes prepared for diffusion assays. FIG. 11a shows a complete layer of basal cells subjacent to layers of partially and terminally differentiated. The configuration represents a stratified in vitro epidermis. FIG. 11b shows a Transmission Electron Micrograph of the outermost layers of cells near or at terminal differentiation; the in vitro stratum corner FIG. 12 shows an area similar to FIG. 11a which has been stained with Nile Red to highlight the presence of epidermal lipids. The images shown in FIGS. 11 and 12 confirm that an in vitro epidermis has been formed and that this has developed barrier properties resembling those of normal skin.

Testing the Skin Health Benefits of the Composition of the Invention Via Assessment of Transepidermal Water Loss (TEWL).

In order to assess the effect of the composition on skin health in dogs Transepidermal Water Loss (TEWL) was used. This parameter indicates the quantity of water that is being lost from the body through the skin at a given time. The amount of water exiting via this route is proportional to the quality and effectiveness of the skin as a barrier. As such, decrease in TEWL is associated with an improvement in Barrier Function.

METHODS

Animals 32 black Labrador retrievers born between Jul. 3, 1990 and Apr. 20, 2000 The thirty-two dogs were split into two groups, a control panel and a test panel. Each group consisted of sixteen dogs. As far as possible the animals were matched between groups for sex and age.

Diet

The dogs were all fed a complete dry food with 100 g of chicken & beef added and mixed in.

The amount of diet fed per day was calculated on an individual animal basis. The calculation used was 110 Kcal× $(Bwt)^{0.75}$. This was used as a guide only; the amounts fed were adjusted as necessary to maintain a stable bodyweight.

Supplement

For the 12 weeks test phase, each dog on the test panel received the composition in the form of a powder. The composition was sprinkled onto the wet component of the food and mixed in.

The composition consisted of the following 5 components at the concentrations given in Table 1.

TABLE 1

Constituents of the composition and the final concentrations used.

| Ingredient | Amount required/400 kcals food (mg) |
|---|---|
| Pantothenic Acid | 20 |
| Nicotinamide | 100 |
| Histidine | 1100 |
| Choline | 300 |
| Inositol | 185 |

The amount of supplement fed to each dog was calculated allowing for the concentrations present in the base diet.

Trial Design

During the week before the pre-feed commenced all dogs were bathed using Greenfields conditioning shampoo. All dogs were bathed again using the same shampoo during the first week of the test phase. All dogs were groomed once a week with a comb for two minutes.

The trial was run for a total of 20 weeks, 8 weeks pre-feed followed by a 12 weeks test phase.

Beginning of Pre-Feed

During the 8 weeks pre-feed the dogs were fed on the complete food. During the first week of the pre-feed, TEWL measurements were taken from all dogs End of Pre-Feed During the last week of the pre-feed TEWL was performed on all dogs Test Phase During the 12 weeks test phase all dogs were fed on the complete food. The test panel also received the composition in the form of a powder. TEWL measurements were taken during weeks 3, 6, 9 and 12 of the test phase.

TEWL Measurements

On each TEWL session 5 readings were taken from each dog using twin probes (providing 10 readings in total) under conditions of consistent temperature and humidity.

A set of TEWL readings was taken from the lower back. The hair was carefully parted in order to provide good contact between the probes and the skin.

The dogs were exercised as normal throughout the trial. On days when TEWL measurements were undertaken the dogs were kept dry until the measurements had been performed.

Veterinary Examinations

All dogs underwent a full veterinary examination prior to starting the trial.

Data Analysis

Comparisons between Transepidermal water loss measurements were performed by two-sample comparison using the Kruskal-Wallis test.

RESULTS

Transepidermal Water Loss (TEWL)

Previous validation work performed with the Dermalab TEWL meter has demonstrated that it is optimal to perform eight readings for a subject on a given site at a given time point in order to stabilise the standard error. Validation has also demonstrated that the most reliable body site for performing TEWL readings is on the back just lateral to the dorsal spine. This location is easily accessible, flat and, assuming the animal is kept away from atmospheric sources of moisture, least likely to become wet (for example due to licking—exogenous forms of moisture on the skin and coat will cause erroneously high readings).

No difference was observed for TEWL values between the control and test panels at the start of the trial or after the eight weeks pre-feed (Table 2). No differences were seen either for any of the groups following 3 and 6 weeks of the test feeding phase. However, after 9 weeks of the test phase a significant difference in TEWL was observed between the test and control group for readings taken on the dorsal back (P=0.048). Following twelve weeks of the test feed (End of trial) a greater difference between the test and control diet for the dorsal spine reading was observed (0.007).

TABLE 2

Transepidermal water loss measurements for feeding trial of the barrier function nutritional supplement.

| | SOP | EOP | 3 week | 6 week | 9 week | EOT |
|---|---|---|---|---|---|---|
| Control Back | 15.43 | 14.05 | 9.66 | 8.16 | 8.38 | 11.55 |
| | 17.88 | 17.94 | 16.66 | 17.81 | 19.13 | 19.83 |
| | (4.75) | (4.18) | (2.86) | (3.01) | (3.37) | (4.1) |
| Test Back | 14.12 | 12.99 | 10.01 | 7.47 | 6.27 | 7.97 |
| | 15.13 | 15.06 | 16.34 | 15.18 | 12.67 | 11.17 |
| | (5.24) | (4.6) | (4.26) | (3.1) | (2.91) | (3.52) |
| P-value (Kruskal-Wallis) | 0.406 | 0.385 | 0.925 | 0.429 | 0.048 | 0.007 |

The values shown are for mean TEWL (normal text), average ranking (based on median, bold text) and standard deviation of the mean (parentheses). Significance of the Kruskal-Wallis analysis is reached at or below 0.05 at the 95% confidence limit. SOP; start of trial, EOP; end of pre-feed, EOT; end of trial. TEWL units are expressed as grams of water loss per body surface area in one hour ($g/m^2.h$).

Data from 2 groups of 16 dogs is illustrated in FIG. 19 wherein; *P<0.05, **P<0.01 between groups SOP/EOPR=start & end of prefeed; 3-12=weeks of supplementation. TEWL; $g/m^2$.hour.

SUMMARY

It has been demonstrated that feeding the composition of the invention can significantly reduce canine transepidermal water loss. A significant improvement in barrier function, as evidenced by reduced TEWL, is first observed following nine weeks of feeding the composition (P<0.05). Barrier function was found to be further improved after a subsequent 3 weeks of the test feed (12 weeks total, P<0.01). It is understood in dermatology that reduced water egress from the skin via TEWL correlates directly with increased epidermal resistance to penetration of environmental agents. This, in turn, will increase the ability of skin to resist disease leading to an improvement of overall health. It is widely accepted that skin disease is a major issue with domestic dogs. Therefore, the provision of this dietary intervention represents a significant step forward in the promotion of natural defences and health in these animals.

The invention claimed is:

1. A method of improving the skin barrier function of a pet comprising administering to the pet a pet foodstuff comprising pantothenic acid, nicotinamide, histidine, inositol and choline wherein pantothenic acid is provided at a level of 10 mg to 500 mg per 400 kcal per day.

2. The method of claim 1 wherein nicotinamide is provided at a level of 25 mg to 800 mg per 400 kcal per day.

3. The method of claim 1 wherein histidine is provided at a level of 10 mg to 10000 mg per 400 kcal per day.

4. The method of claim 1 wherein inositol is provided at a level of 10 mg to 500 mg per 400 kcal per day.

5. The method of claim 1 wherein choline is provided at a level of 10 mg to 700 mg per 400 kcal per day.

6. The method of claim 1, wherein the skin barrier function is improved by increasing the formation of barrier enhancing lipids in the skin of the pet.

7. The method of claim 1 wherein the skin barrier function is improved by reducing the degree of transepidermal water loss.

8. The method of claim 1 wherein said foodstuff further promotes and/or aids the recovery of the skin from disease and/or trauma.

9. The method of claim 1, further comprising administering to the pet one or more of pyridoxine, proline, one or more fatty acids or linoleic acid.

10. The method of claim 1 wherein pyridoxine is provided at a level of 1 mg to 500 mg per 400 kcal per day.

11. The method of claim 1 wherein proline is provided at a level of 0.1 g to 20 g per 400 kcal per day.

* * * * *